United States Patent [19]

Lamborn

[11] 4,403,445
[45] Sep. 13, 1983

[54] METHOD OF SELECTING STRINGLESS BEANS

[75] Inventor: Calvin R. Lamborn, Twin Falls, Id.

[73] Assignee: Sandoz, Ltd., Basel, Switzerland

[21] Appl. No.: 309,590

[22] Filed: Oct. 8, 1981

[51] Int. Cl.³ .............................................. A01H 1/04
[52] U.S. Cl. .................................... 47/58; 47/DIG. 1
[58] Field of Search ........................ 47/1, 58, DIG. 1

[56] References Cited

U.S. PATENT DOCUMENTS 1,756,497 4/1930 Warren .................................... 47/58
3,842,538 10/1974 Barabas .......................... 47/DIG. 1
3,903,645 9/1975 Bradner ......................... 47/DIG. 1

OTHER PUBLICATIONS

Copeland, L. O. "Affinity for Liquids" (Chap. 10 Seed Processing and Handling) *Principles of Seed Science and Tecknology*, Burgess Pub. Co. 1976, p. 250 (only).
Bond, D. A. et al., "Broadbean (Faba Bean)" (Chapt. 10) *Hybridization of Crop Plants*, American Soc. of Agron. et al. 1980 (p. 212 only).

Primary Examiner—James R. Feyrer
Attorney, Agent, or Firm—Robert G. Slick

[57] ABSTRACT

The quality of snap bean seed stock is improved by reducing the number of stringed or hard-point bean plants by selecting out seed which have their placenta attached. This can be done by hand-picking.

2 Claims, 7 Drawing Figures

METHOD OF SELECTING STRINGLESS BEANS

SUMMARY OF THE INVENTION

A few decades ago, all green bean plants had strings along the sutures of their pods and such beans were commonly known as string beans. The strings were strong and objectionable enough to require stripping out before cooking and eating. Over the years plant breeders have selected stringless mutant beans in an effort to develop bean plants which have no objectionable strings and, in fact, the beans are commonly referred to at the present time as snap beans rather than the old terminology string beans. Thus, most beans, throughout the world which are eaten as green beans are of the stringless type.

An unfortunate aspect of the situation is that the beans have a tendency to mutate back to the native type having strings so that it is common to find one or more percent of the plants in a commercial field to have strings in their pods. This quantity of string beans is objectionable and the percentage of beans having strings will increase from year to year if no effort were made to maintain the quality of the stringless seed stock.

The current method to control this problem is to start out with new single plants and increase these to develop new seed stocks. The small lots are often field rogued. A good experienced roguer can recognize some of these undesirable plants with strings. The tip of the pod is stiffer and looks like an eagle claw. These off-type rogues are often called "hard points". At best only a small percent of these stringed beans can be found by eye sight. It is more effective to snip the ends off the pods to find which plants have strings. This method of checking each plant is effective but costly.

When experimenting with different methods to remove flatter bean seed in a companion research program (see U.S. Pat .No. 3,977,525), some unexpected results were observed. In the method based upon the tendency for seed to roll on a slanted moving belt, a significant shift in the number of stringed or hardpoint beans was found. The data are listed below.

| Category of Seed | % of Crop | Frequency of Hard Point Plants |
| --- | --- | --- |
| Rolled twice | 8 | 1 plant in 8 ft. of row |
| Rolled once | 18 | 1 plant in 12 ft. of row |
| Did not roll | 74 | 1 plant in 40 ft. of row |

The evidence was very clear. The seed of string or hard-point plants had been shifted into the rounder seed category. Also evident was the tendency for seed of stringless beans to stay in the category of seed which did not roll.

At the time it was not understood why the shifts had occured; at first it was assumed that perhaps the stringed or hard-point seed was rounder than the rest of the crop.

Plants with stringed or hard-point pods were tagged and harvested separately in order to have seed for further study. When seed from these plants were studied they appeared to be no rounder than seed from the rest of the crop. Yet, they had a greater tendency to roll. There was little question that the difference had to be due to something other than roundness. With this in mind several seeds were examined and the mystery was solved.

The placenta which connects the seed to the bean pod often remains attached to the seed even after threshing and milling. Generally, a fragment of the dorsal suture is still attached to the placenta. The inventor observed that seeds which still had their placenta attached had a definite resistance to rolling. This simple fact seemed to be the solution of why we were shifting the hard-point seed.

It was then theorized that the seed from hardpoint plants would not have their placenta attached after they had been threshed. Seed from hard point plants was examined and only an occasional seed with a placenta was found (three out of 528 seeds). In contrast the presence of the placenta on seed from stringless or non-hard point plants was very common (38% of the seed examined had the placenta). It was also theorized that seed from all varieties of dry edible beans, because they all have strings, would not have their placenta attached. Several pounds of seed of Great Northern, Pinto, Red Mexican, and a white half-runner type were examined. Only one Red Mexican seed was found which still had its placenta attached. Apparently, in string beans grown for use as dry beans, the placenta has a tendency to remain attached to the suture string and remain with the pod tissue during threashing.

Subsequent work proved that the rollability of the seed was influenced by the presence or absence of the placenta. The seed with their placenta attached produced significantly fewer stringed plants (about 1 in 5,000), while the stringed plants were concentrated in the category of seed which did not have their placenta attached (about 1%). The placenta is the tissue by which food and water are transported from the plant to the young developing seed. The vascular system of the placenta is connected with the vascular system in the pod structure. The string is made up of long fiber cells which develop in conjunction with the vascular tissue. The placenta, when removed from the bean pod has the appearance of some fiber cells involved with its attachment. Apparently in stringed beans the cells of the placenta attachment, or its vascular system, develop somewhat intertwined with the suture string, because when the string is present, the placenta tends to remain with the string and the pod.

In contrast, the placenta of stringless beans tends to remain with the seed. The placenta is relatively easily removed from the seed. Threshing, milling, and any subsequent handling tends to knock them off. Normally after milling less then 30% of the placenta are still attached, even when the stringed count is below 1%.

Accordingly, the present invention is based on the discovery that bean seeds with a placenta attached grow into bean plants producing stringless beans. The selection of the desired seed can be made by hand selection.

Various objects and additional features of the invention will appear in the balance of the specification.

DESCRIPTION OF THE PREFERRED EMBODIMENTS

Figure 1:
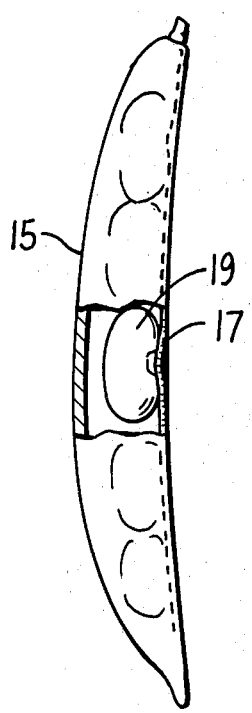
FIG. 1 is a side view of a green bean, partly in section, showing how the seeds are normally attached to the pod.
Figure 2:
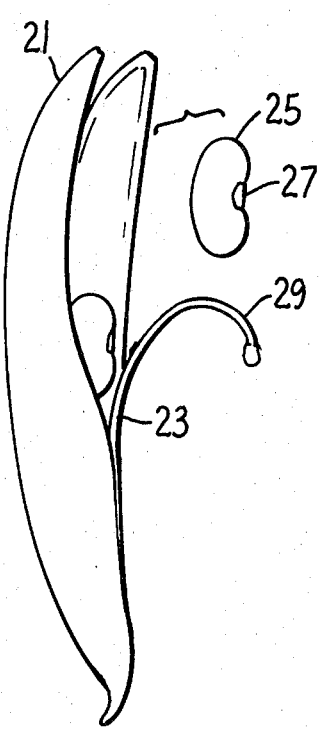
FIG. 2 shows a bean plant wherein the pod is partially opened showing seeds completely detached from the string.

Referring now to the drawings by reference characters, there is shown in FIG. 1 a bean having a pod 15 with a string 17 along one edge of the pod with a plurality of seeds 19 within the pod. In FIG. 2 a bean is shown wherein the pod 21 has been split open to reveal a strong string 23 which adheres with great strength to the pod. The seeds 25 have no placenta attached to the hymen 27. Before the pod of such a bean is edible it would be necessary to forcefully sever the string from the pod as has been done at 29. As was previously pointed out, most green beans do not have strings in their pods such as that shown in FIG. 2.

Figure 3:
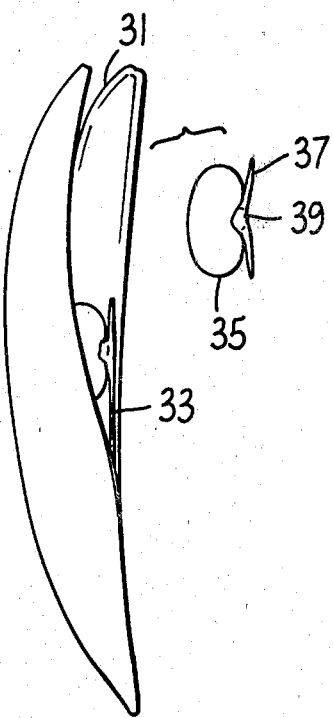
FIG. 3 is a similar view showing a seed detached from the pod wherein the seed has a placenta.

In FIG. 3 a bean is shown with a pod split open as at 31 In this case, the bean has no string present with its vascular system 33. Thus, as a seed 35 is removed from the pod its placenta 37 remains attached to the hymen 39 so that it is as shown in the upper portion of pod 31.

Figure 5:
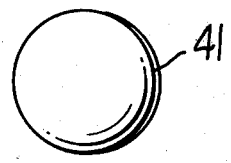
FIG. 5 is an end view of the bean of FIG. 4.
Figure 7:
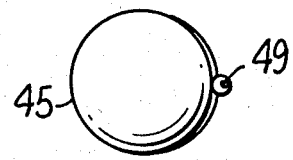
FIG. 7 is an end view of the bean shown in FIG. 6.
Figure 4:
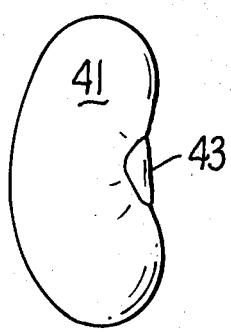
FIG. 4 is a top view of a bean having no placenta.

In FIGS. 4 and 5 the seed 41 has a hymen 43 which is substantially free of any placenta. In contrast, the bean of FIGS. 6 and 7, designated 45, has a hymen 47 to which is attached the placenta 49.

Figure 6:
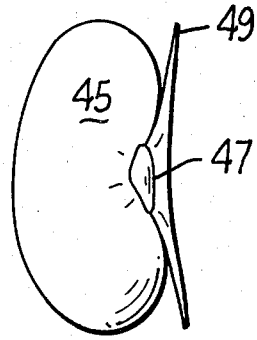
FIG. 6 is a side view of a bean with the placenta attached.

It will be understood that in the figures, and particularly FIGS. 4 through 6, the hymen and the placenta have been exaggerated to illustrate the invention and in actual practice the placenta is very small and is not large enough to cause the beans to feel or taste stringy.

It is entirely possible to improve the bean stock by the hand selection of seed. Thus one can select out those beans such as 35 and 45 having the attached placenta and utilize these seeds for the improvement of the stock.

It has been found that if the bean seeds are soaked in water for one or two minutes, the placenta will absorb water faster than the seed coat. The water greatly expands the placenta and makes it easier for an operator to separate the seeds. After the seeds are separated they are immediately dried. The water soaking is of such short duration that it does not interfere with the subsequent germination of the bean seeds.

The subject matter to be claimed is:

1. A method of improving seed bean stock to increase the percentage of stringless beans therein comprising:
   separating from a lot of bean seeds, those seeds which have a placenta from those seeds which do not have a placenta and maintaining those seeds which have a placenta as improved breeding stock for stringless green beans.
2. The method of claim 1 wherein the bean seed stock is soaked in water for one to two minutes prior to separating.

* * * * *